US009591852B2

(12) United States Patent
Mordas et al.

(10) Patent No.: US 9,591,852 B2
(45) Date of Patent: Mar. 14, 2017

(54) BIOFILM DISRUPTIVE COMPOSITIONS

(75) Inventors: Carolyn J. Mordas, Ewing, NJ (US);
Robert J. Gambogi, Hillsborough, NJ (US)

(73) Assignee: McNeil-PPC, Inc., Skillman, NJ (US)

(*) Notice: Subject to any disclaimer, the term of this patent is extended or adjusted under 35 U.S.C. 154(b) by 566 days.

(21) Appl. No.: 12/623,881

(22) Filed: Nov. 23, 2009

(65) Prior Publication Data
US 2011/0123462 A1 May 26, 2011

(51) Int. Cl.
A61K 8/18 (2006.01)
A61K 31/11 (2006.01)
A61Q 11/00 (2006.01)
A01N 31/02 (2006.01)
A61K 8/34 (2006.01)
A01N 35/02 (2006.01)
A61K 8/30 (2006.01)

(52) U.S. Cl.
CPC ............ A01N 31/02 (2013.01); A01N 35/02 (2013.01); A61K 8/30 (2013.01); A61K 8/342 (2013.01); A61Q 11/00 (2013.01)

(58) Field of Classification Search
None
See application file for complete search history.

(56) References Cited

U.S. PATENT DOCUMENTS

| | | | |
|---|---|---|---|
| 6,121,315 A | 9/2000 | Nair et al. | |
| 6,682,722 B2 | 1/2004 | Majeti et al. | |
| 6,782,307 B2 | 8/2004 | Wilmott et al. | |
| 6,986,901 B2 | 1/2006 | Meisel et al. | |
| 7,025,950 B2 | 4/2006 | Majeti et al. | |
| 2002/0177621 A1* | 11/2002 | Hanada et al. | 514/461 |
| 2003/0202946 A1* | 10/2003 | Hanada et al. | 424/49 |
| 2004/0022743 A1 | 2/2004 | Rosenberg Nevo | |
| 2006/0024244 A1 | 2/2006 | Gebreselassie et al. | |
| 2006/0140884 A1* | 6/2006 | Worrell et al. | 424/58 |
| 2006/0153793 A1 | 7/2006 | Chrisstoffels | |
| 2006/0188468 A1 | 8/2006 | Nguyen et al. | |
| 2006/0193881 A1* | 8/2006 | Bedoukian | 424/405 |
| 2006/0260007 A1 | 11/2006 | Wang et al. | |
| 2007/0065394 A1 | 3/2007 | Pinney | |
| 2007/0140990 A1 | 6/2007 | Fetissova et al. | |
| 2007/0190090 A1 | 8/2007 | Brown | |
| 2008/0140036 A1* | 6/2008 | Buck et al. | 604/360 |
| 2008/0317815 A1 | 12/2008 | Davies | |
| 2010/0172847 A1 | 7/2010 | Modak et al. | |
| 2010/0178256 A1 | 7/2010 | Rosenberg Nevo | |
| 2010/0323939 A1* | 12/2010 | Eng | 510/138 |

FOREIGN PATENT DOCUMENTS

| | | |
|---|---|---|
| EP | 2494959 A1 * | 9/2012 |
| GB | 2153679 | 8/1985 |
| JP | 59029619 | 7/1984 |
| JP | 07316064 | 12/1995 |
| JP | 2000103726 | 4/2000 |
| JP | 2001348308 | 12/2001 |
| JP | 2004018431 | 1/2004 |
| JP | 2007091706 | 4/2007 |
| JP | 2009078988 | 4/2009 |
| WO | 9015597 | 12/1990 |
| WO | WO 200510484 2 A2 * | 11/2005 |
| WO | WO 2005104842 A1 * | 11/2005 |
| WO | WO2006109078 | 10/2006 |
| WO | 2007076446 | 7/2007 |
| WO | WO 2007122792 A2 * | 11/2007 |
| WO | WO2007123271 | 11/2007 |
| WO | WO2008126057 | 10/2008 |
| WO | 2008143889 | 11/2008 |
| WO | 2008157092 | 12/2008 |

OTHER PUBLICATIONS

Kubo, I., Xiao, P., Nihei, K-I, Fujita, K-I., Yamagiwa, Y., Kamikawa, T. Molecular Design of Antifungal Agents. J. Agric. Food Chem., 2002, 50, 3992-3998.*
Kubo, I., Muroi, H., Kubo, A. Structural Functions of Antimicrobial Long-chain Alcohols and Phenols. Bioorganic and Medicinal Chemistry, 1995, 3(7), 873-880.*
Delaquis, P.J., Stanich, K., Girard, B., Mazza, G. Antimicrobial activity of individual and mixed fractions of dill, cilantro, coriander and eucalyptius essential oils. International Journal of Food Microbiology, 2002, 74, 101-109.*
Hongmei Lu, Xianjin Wu, Yizeng Liang, and Jian Zhang. Variation in Chemical Composition and Antibacterial Activities of Essential Oils from Two Species of Houttuynia THUNB. Chem. Pharm. Bull. 54(7) 936-940 (2006).*
Kubo, Bioorganic and Medicinal Chemistry.*
Kubo, Agricultural Chemistry.*
Adam Figiel; Antoni Szumny. Antonio Gutiérrez-Ortîz. Ângel A. Carbonell-Barrachina. Composition of oregano essential oil (Origanum vulgare) as affected by drying method. Journal of Food Engineering 98 (2010) 240-247).*
Davies, David G, et al.; A fatty acid messenger is responsible for including dispersion in microbial biofilms; Journal of Bacteriology; Mar. 2009; vol. 191, No. 5; pp. 1393-1403 (ISSN No. 1098-5530). Alchemist WebPick Awarded by the webzine of ChemWeb.com; Leffingwell & Associates; Odor Properties & Molecular Visualization (Alkenols and Molecular Structures).
Gershon, Herman, et al. "Antifungal Properties of n-Alkanols, a, w-n-Alkanediols, and w-Chloro-a-alkanols," Journal of Pharmaceutical Sciences; vol. 69, No. 4, Apr. 1980, pp. 381-383.
Jacobsson, Jeanette, et al. "A Comparison of pentane-1,5-diol to other diols for use in dermatology," Informa Healthcare, Exprt Opin. Investig. Drugs, (2008), vol. 17(4), pp. 601610.
Tograshi, Naoko, et al., "Antibacterial Activity of Long-Chain Fatty Alcohols against Staphylococcus aureus," Molecules, (2007), vol. 12, pp. 139-148.

(Continued)

Primary Examiner — Frederick Krass
Assistant Examiner — Michael P Cohen

(57) ABSTRACT

In certain embodiments, the present invention relates to compounds, compositions, and methods for disrupting biofilms. In some embodiments, the compounds and compositions comprise unsaturated long chain alcohols and/or aldehydes, or combinations of such compounds. In further embodiments, the present invention contains therapeutic actives to help reduce and/or eradicate the bacteria in the biofilm once the film is disrupted.

10 Claims, No Drawings

(56) References Cited

OTHER PUBLICATIONS

Kabara, Jon J., et al. "Fatty Acids and Derivatives as Antimicrobial Agents," Antimicrobial Agents and Chemotherapy, Jul. 1972, vol. 2, No. 1, American Society for Microbiology, pp. 23-28.

Simões, M., et al. "Effect of cationic surfactants on biofilm removal and mechanical stability,:" International Conference Biofilms (2004): Structure and Activity of Biofilms—Las Vegas, NV, pp. 171-175.

RP Ryan and JM Dow; "Diffusible signals and interspecies communication in bacteria", Microbiology, vol. 154; pp. 1845-1858; 2008.

\* cited by examiner

BIOFILM DISRUPTIVE COMPOSITIONS

FIELD OF INVENTION

In certain embodiments, the present invention relates to compounds, compositions, and methods for disrupting biofilms. In particular embodiments, the present invention relates to the use of unsaturated long chain alcohols and/or aldehydes, or combinations of such compounds in compositions for disrupting biofilms.

BACKGROUND OF THE INVENTION

Biofilms are mucilaginous communities of microorganisms such as bacteria, archaea, fungi, molds, algae or protozoa or mixtures thereof that grow on various surfaces. Biofilms form when microorganisms establish themselves on a surface and activate genes involved in producing a matrix that includes polysaccharides. This matrix may provide protection of biofilm forming bacteria from biocides.

Under certain circumstances, however, biofilms can be undesirable. For example, biofilms can cause damage to equipment such as cooling systems, or aquaculture equipment by corrosion of the equipment by microorganisms residing in the biofilm or by excessive coating or film buildup compromising the normal mechanics of the equipment. Biofilms can also have very detrimental health effects. For example, many hospital-acquired infections involve biofilms, which can contaminate implants and catheters and prevent adequate antimicrobial treatment of such devices. Biofilms also result in adverse health conditions ranging from lung infections as in cystic fibrosis to more prevalent diseases such as tooth decay.

Regarding oral biofilms, certain bacteria can produce highly branched polysaccharides, which together with other microorganisms from the oral cavity form adhesive matrix films facilitating the proliferation of plaque. Left untreated, these oral biofilms can eventually lead to dental caries, gingival inflammation, periodontal disease, and tooth loss. As oral biofilm continues to accumulate, rock-hard white or yellowish deposits can arise. These deposits are called calcified plaque, calculus or tartar, and are formed in the saliva from plaque and minerals, in particular calcium. Established oral biofilm can be very difficult to disrupt whether by mechanical or chemical means. This can be particularly problematic in domains where mechanical removal is not feasible (depending on the implement).

Mechanical removal is an effective methodology used to disperse biofilms. In the case of oral biofilms, toothbrushes, floss, picks, etc. have been used. One limitation of mechanical removal is the ability of the mechanical action to reach the biofilm coated surfaces. This is particularly difficult between teeth and at the tooth/gum line interface.

Another method for preventing or disrupting a biofilm is to interfere with the quorum-sensing signals. Quorum-sensing signals are molecules that help trigger and coordinate part of the process of forming a biofilm. Bacteria constantly secrete low levels of the signals and sense them either through receptors on their surfaces, or internally. The receptors trigger behavioral changes when there are enough bacteria to allow the signals' concentrations to achieve a critical threshold. Once this occurs, bacteria respond by adopting communal behavior, such as forming a biofilm, and in the case of pathogenic bacteria, deploying virulence factors such as toxins. In addition to communicating with members of their own species, bacteria also conduct inter-species communications, such that a biofilm may involve and/or contain more than one species of bacteria. Chemicals have been developed that bind but fail to activate the receptors of quorum-sensing signals or that interfere with signal synthesis. Enzymes that degrade the signals have also been developed.

Strong antimicrobials may be used to kill bacteria in a biofilm, controlling its development and growth. However, once biofilms are established, antimicrobials are not associated with removal of live or dead biofilm. It has been well documented that, because antimicrobials have difficulty penetrating the biofilm's surface layer, they are less effective on bacteria in an established biofilm compared to planktonic bacteria. Agents that help antimicrobials penetrate the biofilm's surface layer improve the effectiveness of the antimicrobials.

Recently, several biofilm dispersing agents have been identified that can be used to signal select bacteria to release from an established biofilm. Signaling agents could help to disperse bacteria, however, signaling compounds have not been shown to be effective on all oral bacterial species, and often need optimized conditions and long contact times to show functionality.

There is, therefore, an ongoing need to identify agents that function as compounds, compositions, and methods for disrupting biofilms. In certain embodiments, the present invention provides certain unsaturated long chain alcohols and/or aldehydes which disrupt biofilms and disperse single and mixed species bacteria from the biofilm.

SUMMARY OF THE INVENTION

In certain embodiments, the present invention is related to compositions, and methods for disrupting biofilms.

In particular embodiments, the present invention comprises a biofilm disruptor comprising at least one unsaturated aliphatic long chain alcohols and/or aldehydes, or combinations of such compounds. In still other embodiments, the present invention may further contain therapeutic actives to facilitate the reduction and/or eradication of bacteria in the biofilm once the film is disrupted.

In one embodiment, the present invention relates to the use as a biofilm disruptor of at least one unsaturated, aliphatic long chain alcohol and/or aldehyde of formula:

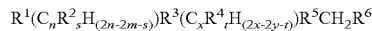

wherein $R^1$ and $R^6$ are, independently, H—, HO—, O=CH—, $CH_3$— or $CH_2$=CH—, (—$OCH_2$—)$_z R^7$, (—$OCH_2CH_2$—)$_z R^7$, (—$OCH_2CH(CH_3)$—)$_z R^7$; $R^2$ and $R^4$ are, independent of themselves and independent of each other, HO—, O=CH—, branched or straight chain $C_1$ to $C_4$ alkyl or alkene, —$CH_2OH$, —$CH_2CH_2OH$; $R^3$ is, independently, single bond or —O—; $R^5$ is, independently, single bond, —O—, (—$OCH_2$—)$_z$, (—$OCH_2CH_2$—)$_z$, (—$OCH_2CH(CH_3)$—)$_z$; $R^7$ is, independent of itself, H—, HO—, O=CH—, $CH_3$— or $CH_2$=CH—; n is an integer from 1 to 10; m (the degree of unsaturation) is an integer from 0 to n/2 if n is even or (n−1)/2 if n is odd; x is an integer from 0 to 10; y (the degree of unsaturation) is an integer from 0 to x/2 if x is even or (x−1)/2 if x is odd and z is an integer from 0 to 5; s is an integer ≤n; and t is an integer ≤x, provided that:
  if neither $R^1$, $R^2$, $R^4$, nor $R^6$ contain any C=C unsaturation, then m+y is at least 1;
  $R^5$ and $R^6$ are not such that $R^5$ is (—$OCH_2$—)$_z$, (—$OCH_2CH_2$—)$_z$, (—$OCH_2CH(CH_3)$—)$_z$, and $R^6$ is (—$OCH_2$—)$_z R^7$, (—$OCH_2CH_2$—)$_z R^7$, (—$OCH_2CH(CH_3)$—)$_z R^7$;

The carbon-carbon chain length from $R^1$ to $R^6$ ranges continuously or intermittently from at least 7, optionally from 8 to 13 carbons, or optionally, from 9 to 12; and at least one of any one of $R^1$, $R^2$, $R^4$ and $R^6$ contains HO— or O=CH—.

In a second embodiment, the present invention relates to a composition for disrupting biofilms, comprising:

i. from about 0.005% to about 10% of a biofilm disruptor comprising at least one unsaturated aliphatic long chain alcohol and/or aldehyde of the formula:

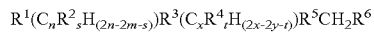

wherein $R^1$ and $R^6$ are, independently, H—, HO—, O=CH—, $CH_3$— or $CH_2$=CH—, (—$OCH_2$—)$_z R^7$, (—$OCH_2CH_2$—)$_z R^7$, (—$OCH_2CH(CH_3)$—)$_z R^7$; $R^2$ and $R^4$ are, independent of themselves and independent of each other, HO—, O=CH—, branched or straight chain $C_1$ to $C_4$ alkyl or alkene, —$CH_2OH$, —$CH_2CH_2OH$; $R^3$ is, independently, single bond or —O—; $R^5$ is, independently, single bond, —O—, (—$OCH_2$—)$_z$, (—$OCH_2CH_2$—)$_z$, (—$OCH_2CH(CH_3)$—)$_z$; $R^7$ is, independent of itself, H—, HO—, O=CH—, $CH_3$— or $CH_2$=CH—; n is an integer from 1 to 10; m (the degree of unsaturation) is an integer from 0 to n/2 if n is even or (n−1)/2 if n is odd; x is an integer from 0 to 10; y (the degree of unsaturation) is an integer from 0 to x/2 if x is even or (x−1)/2 if x is odd and z is an integer from 0 to 5; s is an integer ≤n; and t is an integer ≤x, provided that:

if neither $R^1$, $R^2$, $R^4$, nor $R^6$ contain any C=C unsaturation, then m+y is at least 1;

$R^5$ and $R^6$ are not such that $R^5$ is (—$OCH_2$—)$_z$, (—$OCH_2CH_2$—)$_z$, (—$OCH_2CH(CH_3)$—)$_z$, and $R^6$ is (—$OCH_2$—)$_z R^7$, (—$OCH_2CH_2$—)$_z R^7$, (—$OCH_2CH(CH_3)$—)$_z R^7$;

the carbon-carbon chain length from $R^1$ to $R^6$ ranges continuously or intermittently from at least 7, optionally from 8 to 13 carbons, or optionally, from 9 to 12; and at least one of any one of $R^1$, $R^2$, $R^4$ and $R^6$ contains HO— or O=CH—;

ii. optionally, a therapeutic active; and iii. a carrier selected from the group consisting of a non-oral carrier, pharmaceutically acceptable carrier, orally acceptable carrier and dermatogically acceptable carrier.

In a further embodiment, the present invention relates to an article or device, comprising:

i. an article or device;

ii. from about 0.005% to about 10% of a biofilm disruptor applied to the device or article, the biofilm disruptor comprising at least one unsaturated aliphatic long chain alcohol and/or aldehyde of the formula:

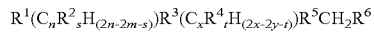

wherein $R^1$ and $R^6$ are, independently, H—, HO—, O=CH—, $CH_3$— or $CH_2$=CH—, (—$OCH_2$—)$_z R^7$, (—$OCH_2CH_2$—)$_z R^7$, (—$OCH_2CH(CH_3)$—)$_z R^7$; $R^2$ and $R^4$ are, independent of themselves and independent of each other, HO—, O=CH—, branched or straight chain $C_1$ to $C_4$ alkyl or alkene, —$CH_2OH$, —$CH_2CH_2OH$; $R^3$ is, independently, single bond or —O—; $R^5$ is, independently, single bond, —O—, (—$OCH_2$—)$_z$, (—$OCH_2CH_2$—)$_z$, (—$OCH_2CH(CH_3)$—)$_z$; $R^7$ is, independent of itself, H—, HO—, O=CH—, $CH_3$— or $CH_2$=CH—; n is an integer from 1 to 10; m (the degree of unsaturation) is an integer from 0 to n/2 if n is even or (n−1)/2 if n is odd; x is an integer from 0 to 10; y (the degree of unsaturation) is an integer from 0 to x/2 if x is even or (x−1)/2 if x is odd and z is an integer from 0 to 5; s is an integer ≤n; and t is an integer ≤x, provided that:

if neither $R^1$, $R^2$, $R^4$, nor $R^6$ contain any C=C unsaturation, then m+y is at least 1;

$R^5$ and $R^6$ are not such that $R^5$ is (—$OCH_2$—)$_z$, (—$OCH_2CH_2$—)$_z$, (—$OCH_2CH(CH_3)$—)$_z$, and $R^6$ is (—$OCH_2$—)$_z R^7$, (—$OCH_2CH_2$—)$_z R^7$, (—$OCH_2CH(CH_3)$—)$_z R^7$;

the carbon-carbon chain length from $R^1$ to $R^6$ ranges continuously or intermittently from at least 7, optionally from 8 to 13 carbons, or optionally, from 9 to 12; and at least one of any one of $R^1$, $R^2$, $R^4$ and $R^6$ contains HO— or O=CH—; and iii. optionally, a therapeutic active applied to the device or article.

In yet another embodiment, the present invention relates to a method of disrupting biofilms, comprising the steps of:

i. providing a surface or substrate comprising a biofilm; and ii. applying to the surface or substrate from about 0.005% to about 10% of a biofilm disruptor comprising at least one unsaturated aliphatic long chain alcohol and/or aldehyde of the formula:

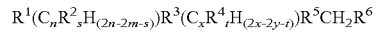

wherein $R^1$ and $R^6$ are, independently, H—, HO—, O=CH—, $CH_3$— or $CH_2$=CH—, (—$OCH_2$—)$_z R^7$, (—$OCH_2CH_2$—)$_z R^7$, (—$OCH_2CH(CH_3)$—)$_z R^7$; $R^2$ and $R^4$ are, independent of themselves and independent of each other, HO—, O=CH—, branched or straight chain $C_1$ to $C_4$ alkyl or alkene, —$CH_2OH$, —$CH_2CH_2OH$; $R^3$ is, independently, single bond or —O—; $R^5$ is, independently, single bond, —O—, (—$OCH_2$—)$_z$, (—$OCH_2CH_2$—)$_z$, (—$OCH_2CH(CH_3)$—)$_z$; $R^7$ is, independent of itself, H—, HO—, O=CH—, $CH_3$— or $CH_2$=CH—; n is an integer from 1 to 10; m (the degree of unsaturation) is an integer from 0 to n/2 if n is even or (n−1)/2 if n is odd; x is an integer from 0 to 10; y (the degree of unsaturation) is an integer from 0 to x/2 if x is even or (x−1)/2 if x is odd and z is an integer from 0 to 5; s is an integer ≤n; and t is an integer ≤x, provided that:

if neither $R^1$, $R^2$, $R^4$, nor $R^6$ contain any C=C unsaturation, then m+y is at least 1;

$R^5$ and $R^6$ are not such that $R^5$ is (—$OCH_2$—)$_z$, (—$OCH_2CH_2$—)$_z$, (—$OCH_2CH(CH_3)$—)$_z$, and $R^6$ is (—$OCH_2$—)$_z R^7$, (—$OCH_2CH_2$—)$_z R^7$, (—$OCH^2CH(CH^3)$—)$_z R^7$;

the carbon-carbon chain length from $R^1$ to $R^6$ ranges continuously or intermittently from at least 7, optionally from 8 to 13 carbons, or optionally, from 9 to 12; and at least one of any one of $R^1$, $R^2$, $R^4$ and $R^6$ contains HO— or O=CH—.

In certain embodiments, this invention is also directed to methods for disrupting biofilms on the surface of living entities and/or non-living things. In other embodiments, the alcohols and/or aldehydes disclosed herein are contacted with the surface of the biofilm in a therapeutically effective amount to disrupt the biofilm, and facilitate the reduction and/or eradication of the bacteria in the biofilm once the film is disrupted.

DETAILED DESCRIPTION OF THE INVENTION

The compositions of the present invention can comprise, consist of, or consist essentially of the essential elements and limitations of the invention described herein, as well any of the additional or optional ingredients, components, or limitations described herein.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All documents cited are, in relevant part, incorporated herein by reference; the citation of any document is not to be construed as an admission that it is prior art with response to the present invention.

The present invention provides compounds, compositions, and methods for disrupting biofilms on the surface of living entities and/or non-living things. The invention also provides methods for removing oral biofilms from the surface of living entities and/or non-living things, and preventing the re-establishment of biofilms by facilitating the reduction and/or eradication of any bacteria before the film can be reestablished.

The term "biofilm" means a mucilaginous community of microorganisms such as bacteria, archaea, fungi, molds, algae or protozoa or mixtures thereof that grow on various surfaces when the microorganisms establish themselves on a surface and activate genes involved in producing a matrix that includes polysaccharides.

The phrase "oral biofilm" means a mixture of bacteria, epithelial cells, leukocytes, macrophages and other oral exudates that forms on the surface of unclean teeth. An oral biofilm can comprise one or more than one species of bacteria.

The phrase "therapeutically effective amount" means the concentration or quantity or level of the compound of the present invention that can attain a particular medical end in disrupting biofilms, such as decreasing biofilm formation, dispersing biofilms, or having toxic activity for biofilms.

The phrase "non-oral and non-dermatological carrier" means that the carrier is not suitable for oral ingestion or application to the surfaces of the oral cavity, skin and/or mucosal surfaces of living organisms including, but not limited to mammals or humans application or ingestion by a mammal without undue toxicity, incompatibility, instability, allergic response, and the like.

The phrase "pharmaceutically acceptable" means that the drugs, medications or inert ingredients which the term describes are suitable for use in humans and lower animals without undue toxicity, incompatibility, instability, irritation, allergic response, and the like.

The phrase "orally acceptable" means that the carrier is suitable for application to the surfaces of the oral cavity or ingestion by a living organism including, but not limited to, mammals and humans without undue toxicity, incompatibility, instability, allergic response, and the like.

The phrase "dermatologically acceptable carrier" means that the carrier is suitable for topical application to the keratinous tissue, has good aesthetic properties, is compatible with the actives of the present invention and any other components, and will not cause any safety or toxicity concerns.

The terms "disrupter", "disruptive" or "disruption" means the partial or complete removal of biofilm or biofilm matrix and/or compromise the integrity of the biofilm.

Biofilm Disruptor

In certain embodiments, the present invention incorporates and/or relates to the use of a biofilm disruptor. The biofilm disruptors of the present invention are or comprise at least one unsaturated aliphatic long chain alcohol or aldehyde of the formula:

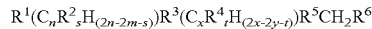

$$R^1(C_nR^2_sH_{(2n-2m-s)})R^3(C_xR^4_tH_{(2x-2y-t)})R^5CH_2R^6$$

wherein $R^1$ and $R^6$ are, independently, H—, HO—, O=CH—, $CH_3$— or $CH_2$=CH—, (—$OCH_2$—)$_z R^7$, (—$OCH_2CH_2$—)$_z R^7$, (—$OCH_2CH(CH_3)$—)$_z R^7$; $R^2$ and $R^4$ are, independent of themselves and independent of each other, HO—, O=CH—, branched or straight chain $C_1$ to $C_4$ alkyl or alkene, —$CH_2OH$, —$CH_2CH_2OH$; $R^3$ is, independently, single bond or —O—; $R^5$ is, independently, single bond, —O—, (—$OCH_2$—)$_z$, (—$OCH_2CH_2$—)$_z$, (—$OCH_2CH(CH_3)$—)$_z$; $R^7$ is, independent of itself, H—, HO—, O=CH—, $CH_3$— or $CH_2$=CH—; n is an integer from 1 to 10; m (the degree of unsaturation) is an integer from 0 to n/2 if n is even or (n−1)/2 if n is odd; x is an integer from 0 to 10; y (the degree of unsaturation) is an integer from 0 to x/2 if x is even or (x−1)/2 if x is odd and z is an integer from 0 to 5; s is an integer ≤n; and t is an integer ≤x, provided that:

if neither $R^1$, $R^2$, $R^4$, nor $R^6$ contain any C=C unsaturation, then m+y is at least 1;

$R^5$ and $R^6$ are not such that $R^5$ is (—$OCH_2$—)$_z$, (—$OCH_2CH_2$—)$_z$, (—$OCH_2CH(CH_3)$—)$_z$, and $R^6$ is (—$OCH_2$—)$_z R^7$, (—$OCH_2CH_2$—)$_z R^7$, (—$OCH_2CH(CH_3)$—)$_z R^7$;

the carbon-carbon chain length from $R^1$ to $R^6$ ranges continuously or intermittently from at least 7, optionally from 8 to 13 carbons, or optionally, from 9 to 12; and at least one of any one of $R^1$, $R^2$, $R^4$ and $R^6$ contains HO— or O=CH—.

In certain embodiments, $R^1$, $R^2$, $R^4$ and $R^6$ are not such that one of $R^1$, $R^2$, $R^4$ and $R^6$ is O=CH— and any other one of $R^1$, $R^2$, $R^4$ and $R^6$ is HO—.

In some embodiments, at least two of any one of, or optionally, at least one of any one of $R^1$, $R^2$, $R^4$ and $R^6$ is HO— or O=CH—. In other embodiments, $R^3$ and $R^5$ are single bonds. In still other embodiments, at least one of any one of $R^1$, $R^2$, $R^4$ and $R^6$ is HO—. In an alternative embodiment, at least one of any one of $R^1$, $R^2$, $R^4$ and $R^6$ is O=CH—.

In certain embodiments, s+t is at least 1. In certain other embodiments, the biofilm disruptor is a linear unsaturated aliphatic long chain alcohol or aldehyde.

In certain embodiments, the biofilm disruptor comprises a compound selected from the group consisting of unsaturated long chain alcohols and/or aldehydes of formulas: $CH_3$ $(C_nR^1_sH_{(2n-2m-s)})CH_2R^2$, $CH_2$=CH$(C_nR^1_sH_{(2n-2m-s)})$ $CH_2R^2$ and mixtures thereof wherein each $R^1$ and $R^2$ are, independent of themselves and independent of each other, H—, HO—, O=CH—, branched or straight chain $C_1$ to $C_4$ alkyl or alkene, —$CH_2OH$, —$CH_2CH_2OH$; and n is an integer from 5 to 11; m is an integer from 1 to 3 and s is an integer ≤n, provided that at least one of any one of $R^1$ and $R^2$ contains HO— or O=CH— and provided that $R^1$ and $R^2$ are not such that one contains O=CH— and the other contains HO—.

In still other embodiments, the biofilm disruptor comprises a compound selected from the group consisting of unsaturated long chain alcohols and/or aldehydes of formulas: $CH_3(C_nR^1_sH_{(2n-2-s)})CH_2R^2$, $CH_2$=CH$(C_nR^1_sH_{(2n-2-s)})$ $CH_2R^2$ and mixtures thereof wherein each $R^1$ and $R^2$ are, independent of themselves and independent of each other, H—, HO—, O=CH—, branched or straight chain $C_1$ to $C_4$ alkyl or alkene, —$CH_2OH$, —$CH_2CH_2OH$; and n is an integer from 5 to 11; and s is an integer ≤n, provided that at least one of any one of $R^1$ and $R^2$ contains HO— or O=CH— and provided that $R^1$ and $R^2$ are not such that one contains O=CH— and the other contains HO—.

In certain other embodiments, the biofilm disruptor is an unsaturated alcohol or aldehyde selected from the group consisting of 1-decen-3-ol; cis-4-decen-1-ol, trans-2-decen-1-ol, cis-2-nonen-1-ol, cis-4-decenal, trans-2-decenal, cis-7-decenal, cis-5-octen-1-ol, trans-2-octen-1-ol, 1-octen-3-ol, cis-3-nonen-1-ol, trans-2-nonen-1-ol, cis-6-nonen-1-ol, 9-decen-1-ol, trans-2-undecen-1-ol, trans-2-dodecen-1-ol, trans-2-octenal, trans-2-nonenal, 6-nonenal, cis-2-decenal, trans-2-undecenal, trans-2-dodecenal, cis-3-octen-1-ol, 3-octen-2-ol, 10-undecen-1-ol, trans-2-tridecen-1-ol, stereoisomers thereof and mixtures thereof.

In other embodiments, the biofilm disruptor is a unsaturated alcohol selected from the group consisting of cis-2-nonen-1-ol, 1-decen-3-ol, stereoisomers thereof and mixtures thereof. In still other embodiments, the biofilm disruptor is 1-decen-3-ol.

In alternative embodiments, the biofilm disruptor is a unsaturated aldehyde selected from the group consisting of trans-2-dodecenal, cis-4-decenal, trans-2-decenal, trans-2-nonenal, trans-2-undecenal, stereoisomers thereof and mixtures thereof. In some embodiments, the biofilm disruptor is an unsaturated aldehyde selected from the group consisting of trans-2-dodecenal, cis-4-decenal, trans-2-decenal, trans-2-nonenal, stereoisomers thereof and mixtures thereof. In other embodiments, the biofilm disruptor is an unsaturated aldehyde selected from the group consisting of trans-2-dodecenal, cis-4-decenal, trans-2-decenal, trans-2-nonenal, stereoisomers thereof and mixtures thereof. In still other embodiments, the biofilm disruptor is a unsaturated aldehyde selected from the group consisting of trans-2-dodecenal, cis-4-decenal, trans-2-decenal, stereoisomers thereof and mixtures thereof.

In certain other embodiments, the present invention also provides methods for disrupting biofilms. In such nonlimiting embodiments, the method comprises contacting a surface or substrate with a therapeutically effective amount of the biofilm disruptors or compositions described above. In certain embodiments of the invention, the surface or substrate is treated with the biofilm disruptors of the present invention by applying the biofilm disruptor onto a surface or substrate so as to leave a residue or deposit of the biofilm disruptor on the surface or substrate that remains of the surface or substrate for at least about 1 (or about 1), optionally 4 (or about 4), optionally 10 (or about 10), optionally 30 (or about 30), optionally 60 (or about 60) or optionally 120 (or about 120) seconds. In some embodiments, the biofilm disruptor is impregnated in a surface in order to inhibit formation of a biofilm on the surface. In alternative embodiments, the biofilm disruptor can be in a copolymer or a gel coating over the surface.

In the case of certain oral care or orally ingestible composition embodiments, the biofilm disruptor of the present invention is present at a level of from 0.005% (or about 0.005%) to 0.5% (or about 0.5%), optionally from 0.01% (or about 0.01%) to 0.3% (or about 0.3%), optionally from 0.025% (or about 0.025%) to 0.2% (or about 0.2%), or optionally from 0.05% (or about 0.05%) to less than 0.1% (or about 0.1%).

In the case of certain composition embodiments for dermatological use and/or for coating onto or disrupting biofilms on non-oral and non-dermatological surfaces, the biofilm disruptor of the present invention is present at a level of from 0.005% (or about 0.005%) to 10% (or about 10%), optionally from 0.01% (or about 0.01%) to 8% (or about 8%), optionally from 0.025% (or about 0.025%) to 6% (or about 6%), or optionally from 0.05% (or about 0.05%) to less than 4% (or about 4%).

Therapeutic Actives

In certain embodiments, the present invention further incorporates or uses in conjunction with the biofilm disruptor an additional therapeutic active. In some embodiments, the active includes, but is not limited to, diffusible signals, antimicrobial actives, anti-inflammatory actives, oral care actives, skin care actives and mixtures thereof.

Diffusible Signals

Diffusible signals are molecules synthesized, released and/or detected by microbial cells as a mechanism for cell-cell communication. Diffusible signals useful in the compositions of the present invention include, but are not limited to, at least one N-acylhomoserine lactones of formula

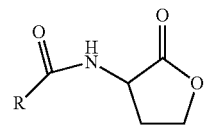

where R is

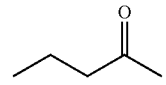

(*V. fischeri* [LuxI]),

(*V. Harveyi* [LuxM]),

(*P. aeruginosa* [RhlI],

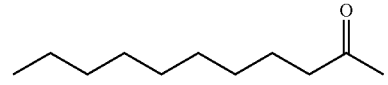

(*P. aeruginosa* [LasI]); at least one autoinducer oligopetides such as

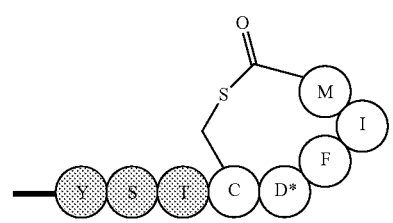

(AIP-I [*S. aureus*]),

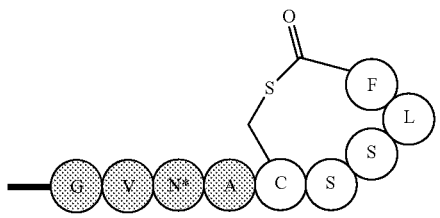

(AIP-II [*S. aureus*]),

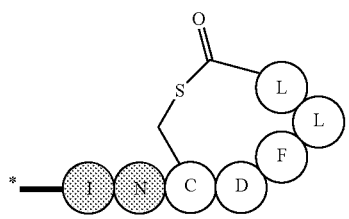

(AIP-III [*S. aureus*]),

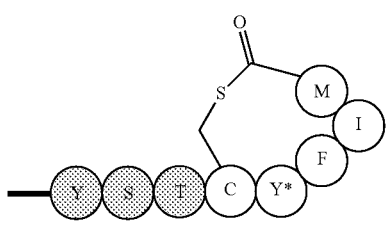

(AIP-IV [*S. aureus*]), ADITROWGD (ComX [*B. subtilis*]), ERGMT (CSF [*B. subtilis*]), EMRLSKFFRDFILQRKK (CSP [*S. pneumonia*]); at least one autoinducer-2 compounds such as

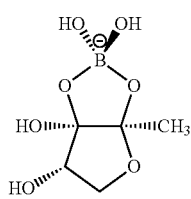

(*V. harveyi* AI-2 molecule) and

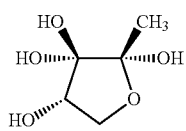

(*S. typhimurium* AI-2 molecule); at least one *Streptomyces butryolactores* such as

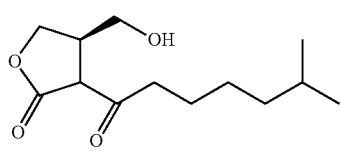 [SMILES: CC(C)CCCCC(=O)C1C(=O)OC[C@H]1CO]

(A-factor [*S. griseus*]); at least one

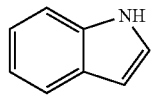

(indole); at least one diketopiperzines such as

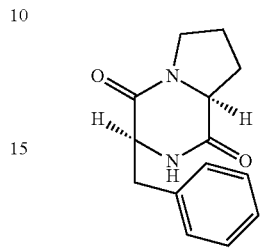

(cyclo(L-Phe-L-Pro) [*P. putida*]) and

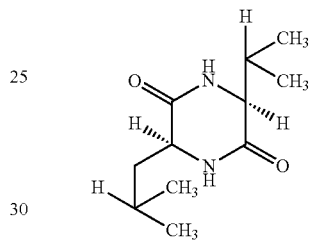

(cyclo(L-Leu-L_Val) [*P. putida*]); at least one diffusible signal factor (DSF) such as, but are not limited to, cis-2-dodecenoic acid (BDSF *B. cenocepacia*]), cis-11-methyl-2-dodecenoic acid (DSF [*X. campestris*]), 12-methyltetradecanoic acid (Xf DSF [*X fastidiosa*]); at least one DSF derivative including, but are not limited to, cis or trans 2-decenoic acid, cis or trans 2-hexenoic acid, cis or trans 2-heptenoic acid, cis or trans 2-octenoic acid, cis or trans 2-nonenoic acid, cis or trans 2-undecenoic acid, cis or trans 2-dodecenoic acid, cis or trans 2-tridecenoic acid, cis or trans 2-tetradecenoic acid, cis or trans 2-pentadecenoic acid, cis or trans 2-hexadecenoic acid, cis or trans 2-heptadecenoic acid, cis or trans 2-octadecenoic acid, cis or trans 2-nonadecenoic acid. Organisms recited above in parentheses describe the organisms that synthesize, release and/or detect the specified signal molecule. A more detailed discussion of DSF or DSF-like compounds can be found in US patent publications US20060260007 to Wang et al. and US20080317815 to Davies, both of which are herein incorporated by reference in their entirety. A more detailed discussion of diffusible signal factors generally can be found in R P Ryan and J M Dow (2008), "Diffusable signals and interspecies communication in bacteria", Microbiology, 154, 1845-1858.

Antimicrobial Actives

Antimicrobial active suitable for use herein include, but are not limited to, triclosan, metronidazole, tetracyclines, quinolones, plant essential oils, camphor, thymol, carvacrol, menthol, eucalyptol, methyl salicylate, tobramycin, cetylpyridinium chloride, neomycin, polymyxin, bacitracin, clindamycin, ciprofloxacin, rifampin, oxfloxacin, macrolides, penicillins, cephalosporins, amoxicillin/clavulanate, quinupristin/dalfopristin, amoxicillin/sulbactum, fluoroquinolones, ketolides, aminoglycosides and mixtures thereof.

Anti-Inflammatory Actives

In certain embodiments, the compositions of the present invention further contain anti-inflammatory actives. Anti-inflammatory actives useful in the present invention include steroidal anti-inflammatory actives, non-steroidal anti-inflammatory actives and mixtures thereof. Suitable steroidal anti-inflammatory include, but not limited to, hydrocortisone, fluocinolone acetonide, halcinonide, halobetasol propionate, clobetasol propionate, betamethasone dipropionate, betamethasone valerate, triamcinolone acetonide and mixtures thereof. Suitable non-steroidal anti-inflammatory actives include, but are not limited to, salicylic acid derivatives such as aspirin, sodium salicylate, choline magnesium salicylate, salsalate, diflunisal, salicylsalicylic acid, sulfasalazine, and olsalazine; para-aminophenol derivatives such as acetaminophen; indole and indene acetic acids such as indomethacin, sulindac, and etodolac; heteroaryl acetic acids such as tolmetin, diclofenac, and ketorolac; arylpropionic acids such as ibuprofen, naproxen, flurbiprofen, ketoprofen, fenoprofen, and oxaprozin; anthranilic acids (fenamates) such as oxicams (piroxicam, tenoxicam), pyrazolidineones (phenylbutazone, oxyphenthatrazone); alkanones such as nabumetone; apazone (azapropazone); nimesulide; and mixtures thereof.

Oral Care Actives

In certain embodiments, the compositions of the present invention further contain oral care actives. In certain embodiments, the oral care actives include, but are not limited to, essential oils (such as menthol, methyl salicylate, eucalyptol, thymol and mixtures thereof), anti-plaque agents, fluoride ion sources such as sodium fluoride, sodium monofluorophosphate, stannous fluoride, and amine fluorides (providing, for example, about 1-5000 ppm of fluoride ion, optionally about 200-1150 ppm of fluoride ion); anti-calculus agents such as water-soluble pyrophosphate salts, preferably alkali metal pyrophosphates; chelating agents; tooth desensitization agents which reduce tooth sensitivity including potassium salts such as potassium nitrate and potassium chloride (for example about 1% to about 5% by weight) and strontium salts such as strontium chloride and strontium acetate (for example about 2% to about 10% by weight); tooth whitening agents and vitamins such as vitamin A.

In certain embodiments, suitable anti-plaque agents include, but are not limited to, non-ionic antibacterial agents such as bromochlorophene and triclosan and cationic agents such as cetylpyridinium chloride and chlorhexidine salts, and mixtures thereof. In general, non-ionic antibacterial agents have a very low solubility in water and have not been incorporated into mouthwash preparations other than those containing high levels of alcohol. Furthermore, it is known that certain water-insoluble flavoring oils such as anethole and menthol have an antibacterial effect at high concentrations. In other embodiments, a major advantage provided by oral care compositions of the present invention is that it allows for the incorporation into non-alcoholic compositions of water-insoluble antibacterial agents and/or water-insoluble anti-calculus agents at effective levels as emulsions or suspensions. In certain embodiments, the oral care compositions of the present invention comprise from about 0.001% to about 1%, optionally from about 0.01% to about 0.5% by weight of a non-ionic antibacterial agent. In some embodiments, the water-insoluble anti-tartar agents comprise zinc salts such as zinc citrate. In certain embodiments, the compositions of the present invention can comprise from about 0.1% to about 1% of a water-insoluble anti-calculus agent.

A more detailed discussion of abrasives, surfactants oral care actives and/or other ingredients useful in the compositions of the present invention can be found in U.S. Pat. No. 7,025,950 to Majeti et al.: U.S. Pat. No. 6,682,722 to Majeti et al.; U.S. Pat. No. 6,782,307 to Wilmott et al. and U.S. Pat. No. 6,121,315 to Nair et al., each of which is herein incorporated by reference in its entirety.

Skin Care Actives

In certain embodiments, the compositions of the present invention further contain skin care actives. In certain embodiments, the oral care actives include, but are not limited to alpha- or beta-hydroxy acids, and derivatives, salts, isomers and tautomers thereof. Non-limiting examples of alpha- and beta-hydroxy acids include salicylic acid, alpha-hydroxy-butyric acid, alpha-hydroxyisobutyric acid, alpha-hydroxyisocaproic acid, alpha-hydroxyisovaleric, atrolactic acid, beta-hydroxybutyric acid, beta-phenyl lactic acid, beta-phenylpyruvic acid, citric acid ethyl pyruvate, galacturonic acid, glucoheptonic acid, glucoheptono 1,4-lactone, gluconic acid, gluconolactone glucuronic acid, glucuronolactone, glycolic acid, isopropyl pyruvate, lactic acid, malic acid, amndelic acid, emthyl pyruvate, mucic acid, pyruvic acid, saccharic acid, saccharic acid 1,4-lactone, tartaric acid and tartronic acid, and mixtures thereof.

Carriers

In certain embodiments, the fatty alcohols of the present invention are further mixed with appropriate carrier materials or ingredients to form desired dosage forms. In some embodiments, the fatty alcohols and compositions described herein may prepared as unitary dosage forms suitable for administration orally, percutaneously, by parenteral injection (including subcutaneous, intramuscular, intravenous and intradermal), topically, intranasally, by inhalation, or for application to a medical device, such as an implant, catheter, or other device.

For pharmaceutically acceptable carriers that permit parenteral administration, the pharmaceutically acceptable carriers often comprise sterile water, which may be supplemented with various solutes to, for example, increase solubility. Injectable solutions may be prepared in which the pharmaceutically acceptable carrier comprises saline solution, glucose solution, or a mixture thereof, which may include certain well-known anti-oxidants, buffers, bacteriostats, and other solutes that render the formulation isotonic with the blood of the intended patient.

For pharmaceutically acceptable carriers that permit intranasal administration, the pharmaceutically acceptable carriers often comprise poly acrylic acids such as Carbopol® 940, a hydrogenated castor oil such as Cremophor® RH40, glycerol, vinylpyrrolidones such as PVP-K90® or PVP K30®, polyethylene glycols such as PEG 1450®, benzyl alcohol, Edetate sodium, hydroxycellulose, potassium chloride, potassium phosphate, and sodium phosphate. In some embodiments, the compositions used for intranasal administration also commonly include benzalkonium chloride as an anti-microbial preservative.

For pharmaceutically acceptable carriers that permit administration by inhalation, the pharmaceutically acceptable carriers often comprise solvent/carrier/water mixtures that are easily dispersed and inhaled via a nebulizer or inhaler. In some embodiments, for example, a mixture of ethanol/propylene glycol/water in the ratio of about 85:10:5 (parts ethanol: parts propylene glycol: parts water) can be used to administer the compounds and compositions of the invention via inhalation.

For orally acceptable carriers, the orally acceptable carrier may be in the form of a mouthrinse, toothpaste, toothgel, dentifrice, breath spray, or prophylaxis paste, and comprise at least about 24%, optionally, at least about 60%, optionally, at least about 80% to about 99%, or, optionally, at least about 80% to about 90% by weight of a liquid carrier. In certain embodiments, the liquid carrier may be in the form of a solution, emulsion or microemulsion of components and, in some embodiments, contain at least about 5% by weight water, optionally, at least about 10% by weight water. In certain embodiments, alcohol such as ethanol may optionally form part of the liquid carrier, for example, from about 5% to about 35% by weight of the liquid carrier, and, in some embodiments, is particularly useful in oral care compositions having a high flavor impact and breath-freshening and/or antiseptic properties.

In certain embodiments, the oral composition may also be in the form of chewing gum, a breath strip, a lozenge, or a breath mint containing or coated with a biofilm disruptor composition.

In other embodiments, the orally acceptable carriers are suspensions, syrups, elixirs and solutions. In alternate embodiments, the orally acceptable carriers are solid carriers containing or coated with the long chain alcohols, aldehydes or combinations thereof, including, but not limited to, toothpowders, powders, whitening strip, breath strip, lozenge, pills, capsules, suppositories and tablets. In still other embodiments, the solid carriers can be prepared so as to be suitable for rectal or vaginal application.

In certain embodiments, the pH of the oral care compositions according to the present invention is generally in the range of from about 3.5 to about 9.0, optionally, from about 4.0 to 8.0, or optionally, from about 4.0 to about 7.0. In other embodiments, if desired, the pH can be controlled with acid, for example citric acid, or base, for example sodium hydroxide, or buffered, for example with citrate, phosphate, benzoate or bicarbonate buffering salts.

In certain orally administered embodiments, sweeteners can be used including, but not limited to, sucralose, aspartame, acesulfam K, saccharin, cyclamate and mixtures thereof.

Methods of Using the Biofilm Disruptors

In certain embodiments, the biofilm disruptors are used to treat articles, devices, substrates and surfaces (mammalian or inanimate) to disrupt the formation of or disrupt already formed biofilms.

In some embodiments, the surface to be treated with the biofilm disruptors includes medical devices such as catheters, respirators, and ventilators. In other embodiments, the surface can be that of implanted medical devices, including stents, artificial valves, joints, pins, bone implants, sutures, staples, pacemakers, and other temporary or permanent medical devices.

In other embodiments, the surface to be treated with the biofilm disruptors includes articles such as drains, tubs, kitchen appliances, countertops, shower curtains, grout, toilets, industrial food and beverage production facilities, flooring, and food processing equipment and the like.

The surface to be treated with biofilm disruptors in yet another embodiment includes article surfaces such as filter or heat exchanger surfaces, providing means for reducing and/or eliminating biofouling of heat exchangers or filters.

Other embodiments of the present invention, relate to use on or application of the biofilm disruptors to articles, devices, substrates or surfaces associated marine structures including, but not limited to, boats, piers, oil platforms, water intake ports, sieves, and viewing ports.

In certain embodiments, the articles, substrate or device surface being treated with the biofilm disruptors can alternatively be associated with a system for water treatment and/or distribution (like drinking water treatment and/or distributing systems, pool and spa water treatment systems, water treatment and/or distribution systems in manufacturing operations, and a system for dental water treatment and/or distribution). In some embodiments, the biofilm disruptor treated article, substrate or device surface can also be associated with a system for petroleum drilling, storage, separation, refining and/or distribution (like petroleum separation trains, a petroleum container, petroleum distributing pipes, and petroleum drilling equipment). In other embodiments, the biofilm disruptor can also be included in formulations directed at reducing or eliminating biofilm deposits or biofouling in porous medium, such as with oil and gas bearing geological formations. In particular embodiments, the biofilm disruptor treatment may be accomplished by applying a coating of the biofilm disruptor, such as by painting, to the surface of articles, substrate or device.

In still other embodiments, the present invention further relates to a method of using the biofilm disruptors to treat and/or prevent dental plaque, dental carries, gingival disease, periodontal disease, and oral infection in a subject. In such nonlimiting embodiments, the method involves treating the surfaces of the oral cavity of the subject with the biofilm disruptor according to the present invention. In particular embodiments, treatment can be carried out with a dentifrice, mouthwash, mouth rinse, dental floss, gum, strip, toothpaste, a toothbrush containing the biofilm disruptor, and other preparations containing the biofilm disruptor. In certain other embodiments, the composition may also contain other compounds known in the dental arts that are typically added to dental compositions. For example, in some embodiments, the biofilm disruptor composition may also include such oral care actives as fluoride, desensitizing agents, anti-tartar agents, anti-bacterial agents, remineralization agents, whitening agents, abrasives and anti-caries agents.

In other embodiments, the biofilm disruptor is used with a dental device or article that is placed in the oral cavity. The biofilm disruptor is coated on, encapsulated in, or impregnated in the dental article/device. Suitable dental articles/devices include, but are not limited to, dentures, dental dams, and certain types of orthodontic braces. Additional components or ingredients may be included in or with the biofilm disruptor.

In certain other embodiments, the dental article is a dental floss. Any fiber known in the art may be used in the dental floss. Suitable fibers include polyamides (such as nylon), polyesters, polypropylenes, polytetrafluoroethylenes, cellulose, and cotton. The biofilm disruptor composition may be impregnated into the fiber, coated on the fiber, or otherwise incorporated into the dental floss. In some embodiments, the dental floss may be coated or impregnated with a wax or other hydrophobic substance for ease of use during the flossing process. Suitable waxes include microcrystalline waxes, beeswax, paraffin waxes, carnauba waxes, and polyethylene waxes. In certain embodiments, the biofilm disruptor composition may be coated onto the dental floss as part of the wax layer, as a second or additional layer in conjunction with the wax layer, or applied to the fiber as discussed above.

In certain embodiments, the dental article may be a toothpick that is impregnated with or coated with the biofilm disruptor composition. In some embodiments, the toothpicks may be made from natural products, such as wood, or artificial components, including various plastics.

In certain embodiments, the dental article may also be a dental appliance such as a dental aspirator, bite block, dental dam, tongue stabilizer, tongue deflector, or any other piece of dental equipment that a dentist or dental assistant may use in the mouth of a patient. The portion of the dental appliance that comes into contact with the oral cavity of a patient may be coated with the biofilm disruptor composition.

The dental article may also be a dental construct, such as a veneers, crowns, inlays, onlays, or bridges that are placed on the teeth. Dental constructs are typically made of metal alloys, porcelain, ceramic, amalgam, acrylate polymers, or a combination of these materials. The biofilm disruptor composition may be embedded in the composition used to make the dental construct. Alternatively, the biofilm disruptor composition may be coated on the dental construct after it has been prepared.

In some embodiments, the biofilm disruptor may be incorporated into the various parts of a toothbrush by means known in the art. For instance, in particular embodiments, the biofilm disruptor composition may be contained in the tuft holes of the toothbrush. Alternatively, in other embodiments, the biofilm disruptor composition may be coated or embedded in the bristles of the toothbrush. Optionally, other parts of the toothbrush may also be coated or embedded with the biofilm disruptor composition, including any parts of the toothbrush that supplement the bristles and are designed to be contacted with the oral cavity. In certain embodiments, toothbrushes may contain rubber paddles, tongue cleaners, or other pieces extended from the head for the purposes of being contacted with the tooth, tongue, gums, or other areas of the oral cavity. In such embodiments, these parts may be embedded with the biofilm disruptor composition and, optionally, a surfactant, biocide, and/or other additive.

In certain embodiments, the biofilm disruptor may also be incorporated into or used to form an encapsulated system to allow for a controlled release. In these embodiments, the biofilm disruptor composition can optionally be in the form of a plurality of small microspheres that encapsulate the biofilm disruptor. The microspheres can optionally have an outer coating of dissolvable material that enables the biofilm disruptor to slowly release over repeated brushings.

In certain embodiments, the present invention also relates to a method of cleaning and/or disinfecting articles such as contact lenses. The method of these embodiments involves treating contact lenses with a cleaning and/or disinfecting solution containing the biofilm disruptor according to the present invention. In some embodiments, the contact lens may be treated in this manner while being stored in solution or while being used in vivo. In alternative embodiments, the biofilm disruptor can be used in eye drops.

In certain embodiments, the present invention further relates to a method of treating and/or preventing acne or other biofilm-associated skin infections on the skin of a subject. The methods of these embodiments involve treating the skin of the subject systemically or the skin surface topically with the biofilm disruptor according to the present invention under conditions effective to treat and/or prevent the acne or biofilm-associated skin infections. In some embodiments, the biofilm disruptor may be present in an ointment, cream, liniment, salves, shaving lotion, or aftershave. In these embodiments, the biofilm disruptor may also be present in a powder, cosmetic, ointment, cream, liquid, soap, gel, suspension, lotion, solution, paste, spray, aerosol, oil, cosmetic applicator, and/or solid, woven or non-woven material intended to contact or be proximate with the skin. In other embodiments, biofilm disruptor may be present in suspensions, syrups, elixirs, solutions, pills, capsules, suppositories and tablets for oral systemic use.

In certain embodiments, the present invention also relates to a method of treating and/or preventing a chronic biofilm-associated disease in a subject. The methods of these embodiments involve administering to the subject the biofilm disruptor according to the present invention under conditions effective to treat and/or prevent the chronic biofilm-associated disease. The chronic biofilm-associated diseases to be treated and/or prevented include, but are not limited to, middle ear infections, osteomyelitis, prostatitis, colitis, vaginitis, urethritis, arterial plaques, sinovial infections, infections along tissue fascia, respiratory tract infections (e.g., infections associated with lung infections of cystic fibrosis patients, pneumonia, pleurisy, pericardial infections), genito-urinary infections, and gastric or duodenal ulcer infections. In some embodiments, the biofilm disruptor may be administered in combination with the antimicrobial actives described above. In one embodiment, the biofilm disruptor and the antimicrobial treatment are administered simultaneously. In another embodiment, the biofilm disruptor and antimicrobial treatment are administered separately. In the case of gastric therapies, gastrointestinal actives may also be employed as described in U.S. Pat. No. 6,986,901 to Meisel et al., herein incorporated by reference in its entirety.

The biofilm disruptor can be impregnated in a surface in order to inhibit formation of a biofilm on the surface. Alternatively, the biofilm disruptor can be in a copolymer or a gel coating over the surface.

In certain embodiments, the present invention further relates to kits comprising the biofilm disruptor and instructions on the use of the biofilm disruptor with the packages containing the biofilm disruptor or with other forms of advertising associated with the sale or use of the biofilm disruptor. In certain embodiments, the instructions may be included in any manner typically used by consumer product manufacturing or supply companies. Nonlimiting examples include providing instructions on a label attached to the container holding the compounds and/or compositions; on a sheet either attached to the container or accompanying it when purchased; or in advertisements, demonstrations, and/or other written or oral instructions which may be connected to the purchase or use of the compounds and/or compositions.

In particular embodiments, the instructions will include a description of the use of the biofilm disruptors. In these embodiments, the instructions, for instance, may additionally include information relating to the recommended amount of compounds and/or compositions to apply to the substrate.

The compounds and compositions described herein can be prepared by conventional organic syntheses, readily available to one of ordinary skill in the art without undue experimentation. Specific examples are described herein below.

EXAMPLES

Example 1

Screening of Biofilm Disruptive Agents

Formulations containing unsaturated long chain alcohols as the biofilm disruptive agents were prepared according to the following formula:

| Raw material | % (w/v) |
| --- | --- |
| Water | 77.75 |
| Ethanol (190 proof) | 22 |
| Unsaturated long chain alcohol | 0.05 |
| Pluronic F-127 | 0.2 |

Separate formulations were prepared from the above ingredients with each formulation containing one of the unsaturated long chain alcohols in Table 1. The formulations were then tested as indicated below. In addition, the following negative control without any unsaturated long chain alcohol was also prepared.

| Raw material | % (w/v) |
| --- | --- |
| Water | 77.80 |
| Ethanol (190 proof) | 22 |
| Pluronic F-127 | 0.2 |

A 48-hour salivary biofilm was grown on a polystyrene peg plate substrate (96 pegs, N=8 per test group). The pegs were subsequently treated for twenty minutes with each of the long chain alcohols formulations described above, as well as the negative control. After treatment, viable bacteria remaining on the substrate were removed by sonication using a Ultrasonic processor XL by Misonix (Farmingdale, N.Y.), lysed with Celsis Luminex (Celsis Rapid Detection Rapiscreen (Celsis International PLC, Chicago)) and ATP from the bacteria were measured using a bioluminescence marker Celsis LuminATE (Celsis Rapid Detection Rapiscreen (Celsis International PLC, Chicago)). Data was reported in log RLU (relative light units), where decreasing log RLUs indicates fewer bacteria remaining on the substrate and in M-factor units where M-factor is the difference between the log RLU values of the compound tested and the negative control. The results of the test are shown on Table 1.

TABLE 1

Biofilm treatment test results

| Unsaturated Long Chain Alcohol | Supplier Information | log RLU compound | log RLU negative control | M-factor |
| --- | --- | --- | --- | --- |
| cis-2-hexen-1-ol | Sigma-Aldrich St. Louis, MO 63103 | 5.21 | 5.32 | 0.11 |
| cis-3-hexen-1-ol | TCI America Portland, OR 97203 | 5.22 | 5.28 | 0.06 |
| trans-2-hexen-1-ol | SAFC (Sigma Aldrich) St. Louis, MO 63103 | 5.20 | 5.32 | 0.12 |
| cis-3-hepten-1-ol | SAFC (Sigma Aldrich) St. Louis, MO 63103 | 5.07 | 5.32 | 0.25 |
| cis-5-octen-1-ol, | SAFC (Sigma Aldrich) St. Louis, MO 63103 | 5.01 | 5.32 | 0.31 |
| trans-2-octen-1-ol | Sigma-Aldrich St. Louis, MO 63103 Alfa Aesar Ward Hill, MA 01835 | 4.89 | 5.58 | 0.69 |
| 1-octen-3-ol | Acros Organics US Distributor: Morris Plains, NJ 07950 | 4.99 | 5.32 | 0.33 |
| cis-2-nonen-1-ol | SAFC (Sigma Aldrich) St. Louis, MO 63103 | 4.57 | 5.33 | 0.76 |
| cis-3-nonen-1-ol | Sigma-Aldrich St. Louis, MO 63103 | 4.56 | 5.32 | 0.76 |
| cis-6-nonen-1-ol | SAFC (Sigma Aldrich) St. Louis, MO 63103 | 4.60 | 5.32 | 0.72 |
| trans-2-nonen-1-ol | SAFC (Sigma Aldrich) St. Louis, MO 63103 | 4.83 | 5.28 | 0.45 |
| cis-4-decen-1-ol | Sigma-Aldrich St. Louis, MO 63103 | 4.71 | 5.33 | 0.62 |
| trans-2-decen-1-ol | Sigma-Aldrich St. Louis, MO 63103 | 4.13 | 5.58 | 1.45 |
| 9-decen-1-ol | Sigma-Aldrich St. Louis, MO 63103 | 4.35 | 5.32 | 0.97 |
| 1-decen-3-ol | SAFC (Sigma Aldrich) St. Louis, MO 63103 | 4.46 | 5.32 | 0.86 |
| trans-2-dodecen-1-ol | Fluka (Sigma-Aldrich) St. Louis, MO 63103 | 4.44 | 5.32 | 0.88 |
| trans-2-undecen-1-ol | Alfa Aesar Ward Hill, MA 01835 | 4.72 | 5.28 | 0.56 |

Table 1 shows that unsaturated alcohols of chain length of at least 7 carbons resulted in an activity difference versus the negative control (M-factor) of greater than 0.21.

Example 2

Screening of Biofilm Disruptive Agents

Formulations containing long chain aldehydes as the biofilm disruptive agents were prepared according to the following formula:

| Raw material | % (w/v) |
| --- | --- |
| Water | 77.75 |
| Ethanol (190 proof) | 22 |
| Unsaturated long chain aldehyde | 0.05 |
| Pluronic F-127 | 0.2 |

Separate formulations were prepared from the above ingredients with each formulation containing one of the unsaturated long chain aldehydes in Table 2. The formulations were then tested as indicated below. In addition, the following negative control without any unsaturated long chain aldehyde was also prepared.

| Raw material | % (w/v) |
|---|---|
| Water | 77.80 |
| Ethanol (190 proof) | 22 |
| Pluronic F-127 | 0.2 |

A 48-hour salivary biofilm was grown on a polystyrene peg plate substrate (96 pegs, N=8 per test group). The pegs were subsequently treated for twenty minutes with each of the long chain alcohols formulations described above, as well as the negative control. After treatment, viable bacteria remaining on the substrate were removed by sonication using a Ultrasonic processor XL by Misonix (Farmingdale, N.Y.), lysed with Celsis Luminex (Celsis Rapid Detection Rapiscreen (Celsis International PLC, Chicago)) and ATP from the bacteria were measured using a bioluminescence marker. Celsis LuminATE (Celsis Rapid Detection Rapiscreen (Celsis International PLC, Chicago)). Data was reported in log RLU (relative light units), where decreasing log RLUs indicates fewer bacteria remaining on the substrate and in M-factor units where M-factor is the difference between the log RLU values of the compound tested and the negative control. The results of the test are shown on Table 2.

TABLE 2

Biofilm Treatment Test Results

| Unsaturated Long Chain Aldehyde | Supplier Information | log RLU compound | log RLU negative control | M-factor |
|---|---|---|---|---|
| trans-2-hexenal | SAFC (Sigma Aldrich) St. Louis, MO 63103 | 5.39 | 5.58 | 0.19 |
| trans-2-heptenal | SAFC (Sigma Aldrich) St. Louis, MO 63103 | 5.52 | 5.58 | 0.06 |
| cis-4-hepten-1-al | TCI America Portland, OR 97203 | 5.14 | 5.10 | −0.04 |
| 2,6-dimethyl-5-hepten-1-al | TCI America Portland, OR 97203 | 5.07 | 5.28 | 0.21 |
| trans-2-octenal | SAFC (Sigma Aldrich) St. Louis, MO 63103 | 5.26 | 5.58 | 0.32 |
| trans-2-nonenal | SAFC (Sigma Aldrich) St. Louis, MO 63103 | 4.66 | 5.58 | 0.92 |
| cis-6-nonenal | Alfa Aesar Ward Hill, MA 01835 | 4.84 | 5.28 | 0.44 |
| cis-4-decenal | SAFC (Sigma Aldrich) St. Louis, MO 63103 | 4.59 | 5.58 | 0.99 |
| cis-7-decenal | Sigma Aldrich St. Louis, MO 63103 | 5.25 | 5.58 | 0.33 |
| trans-2-decenal | Fluka (Sigma Aldrich) St. Louis, MO 63103 | 4.63 | 5.58 | 0.95 |
| trans-2-undecenal | SAFC (Sigma Aldrich) St. Louis, MO 63103 | 4.49 | 5.32 | 0.83 |
| trans-2-dodecenal | SAFC (Sigma Aldrich) St. Louis, MO 63103 | 4.58 | 5.58 | 1.00 |

Table 2 shows that unsaturated aldehydes of chain length of at least 7 carbons resulted in an activity difference versus the negative control (M-factor) of greater than 0.21.

Example 3

Concentration Dependence of Biofilm Disruptor Activity

To determine the concentration dependence of biofilm disruptor activity, a series of formulations was prepared with cis-2-nonen-1-ol concentration ranging from 0.0005% to 0.1%. These formulations were tested against the negative control in the biofilm disruption screening assay described in Examples 1 and 2. Data was reported in log RLU (relative light units) where decreasing log RLUs indicates fewer bacteria remaining on the substrate and in M-factor units where M-factor is the difference between the log RLU values of the compound tested and the negative control. The results of the test are shown on Table 3.

TABLE 3

Biofilm treatment results as a function of concentration for cis-2-nonen-1-ol.

| Raw material | A % (w/v) | B % (w/v) | C % (w/v) | D % (w/v) | E % (w/v) | F % (w/v) | G % (w/v) | Negative control % (w/v) |
|---|---|---|---|---|---|---|---|---|
| Water | 77.7 | 77.75 | 77.775 | 77.79 | 77.795 | 77.799 | 77.7995 | 77.8 |
| Ethanol (190 proof) | 22 | 22 | 22 | 22 | 22 | 22 | 22 | 22 |
| cis-2-nonen-1-ol | 0.1 | 0.05 | 0.025 | 0.01 | 0.005 | 0.001 | 0.0005 | 0 |
| Pluronic F-127 | 0.2 | 0.2 | 0.2 | 0.2 | 0.2 | 0.2 | 0.2 | 0.2 |
| log RLU | 4.81 | 4.82 | 5.28 | 5.59 | 5.69 | 5.70 | 5.72 | 5.63 |
| M-factor | 0.82 | 0.82 | 0.35 | 0.04 | −0.06 | −0.07 | −0.09 | NA |

These results indicate that biofilm disruption improves (i.e., M-factor increases) with increasing concentration of the biofilm disruptor.

Example 4

Combinations of Long-Chain Alcohols

To further evaluate the potential of combining two biofilm disruptive agents, the following formulations containing cis-2-nonen-1-ol and cis-6-nonen-1-ol were prepared. These formulations were tested against the negative control in the biofilm disruption screening assay described in Examples 1 and 2. Data was reported in log RLU (relative light units) where log RLUs indicates the amount of bacteria remaining on the substrate. The results of the test are shown on Table 4.

TABLE 4

Biofilm treatment results in blends of cis-2-nonen-1-ol and cis-6-nonen-1-ol.

| Raw material | A % (w/v) | B % (w/v) | C % (w/v) | D % (w/v) | E % (w/v) |
|---|---|---|---|---|---|
| Water | 77.75 | 77.75 | 77.75 | 77.75 | 77.75 |
| Ethanol (190 proof) | 22 | 22 | 22 | 22 | 22 |
| cis-2-nonen-1-ol | 0.05 | 0.01 | 0 | 0.04 | 0.025 |
| cis-6-nonen-1-ol | 0 | 0.04 | 0.05 | 0.01 | 0.025 |
| Pluronic F-127 | 0.2 | 0.2 | 0.2 | 0.2 | 0.2 |
| log RLU | 4.75 | 4.86 | 4.78 | 4.9 | 4.81 |

Table 4 indicates effectiveness (i.e., similarly reduced log RLU values) of using either individual biofilm disruptors or combinations of the biofilm disruptors.

Example 5

Combinations of Biofilm Disruptors and Antimicrobial Actives

The following formulations containing antimicrobial actives (menthol, thymol, eucalyptol, and methyl salicylate) were prepared and evaluated in a flow-through biofilm model to evaluate potential for oral plaque disruption following a thirty-second treatment.

Wildtype organisms harvested from human saliva inoculate media flowing past pegs on a 96-peg polystyrene plate where organisms adhere and develop into biofilms. The biofilms are treated twice a day for a total of five treatments over the course of 60 hours.

Data was reported in log RLU (relative light units) where decreasing log RLUs indicates fewer bacteria remaining on the substrate. The results of the test are shown on Table 4.

TABLE 5

Biofilm treatment results of blends of cis-2-nonen-1-ol and 1-decen-3-ol in formulations containing anti-microbial agents (menthol, thymol, eucalyptol, and methyl salicylate).

| Raw material | A (% w/v) | B (% w/v) | C (% w/v) |
|---|---|---|---|
| L-Menthol, USP | 0.042 | 0.042 | 0.042 |
| Thymol NF | 0.064 | 0.064 | 0.064 |
| Methyl Salicylate NF | 0.066 | 0.066 | 0.066 |
| Eucalyptol USP | 0.092 | 0.092 | 0.092 |
| Pluronic F-127 NF Prill | 0.250 | 0.250 | 0.250 |
| Benzoic Acid | 0.128 | 0.120 | 0.120 |
| Sodium Benzoate | 0.026 | 0.0354 | 0.0354 |
| Sodium saccharin | 0.020 | 0.117 | 0.117 |
| Sucralose | 0.041 | 0 | 0 |
| FD&C Green No. 3 | 0.0005 | 0.0005 | 0.0005 |

TABLE 5-continued

Biofilm treatment results of blends of cis-2-nonen-1-ol and 1-decen-3-ol in formulations containing anti-microbial agents (menthol, thymol, eucalyptol, and methyl salicylate).

| Raw material | A (% w/v) | B (% w/v) | C (% w/v) |
|---|---|---|---|
| Sorbitol 70%, USP | 20.0 | 20.0 | 20.0 |
| Alcohol, 190 proof | 21.6 (% v/v) | 21.6 (% v/v) | 21.6 (% v/v) |
| Flavor | 0.12 | 0.085 | 0.085 |
| cis-2-nonen-1-ol | 0.05 | 0 | 0 |
| 1-decen-3-ol | 0 | 0.05 | 0 |
| Purified Water | 79.1 | 79.1 | 79.1 |
| TOTAL | 100 | 100 | 100 |
| log RLU | 4.46 | 4.36 | 4.75 |

Formulations A and B, containing biofilm disrupting agents cis-2-nonen-1-ol and 1-decen-3-ol respectively, results in reduced biofilm remaining on the substrate (i.e., decreased log RLU) when compared to the Formulation C control (log RLU=4.75).

Various embodiments of the invention have been set forth above. Each embodiment is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents.

What is claimed is:

1. A composition comprising:
   i. from about 0.005% to less than 0.5% of a biofilm disruptor selected from the group consisting of 1-decen-3-ol, cis-2-nonen-1-ol, and mixtures thereof; and
   ii. an orally acceptable carrier in the form of a mouthwash, mouthrinse, toothpaste, tooth gel, dentifrice, breath spray, prophylaxis paste, chewing gum, breath strip, lozenge, or breath mint.

2. The composition according to claim 1, wherein the biofilm disruptor is 1-decen-3-ol.

3. The composition of claim 1 wherein said carrier is in the form of a mouthwash or mouthrise.

4. The composition of claim 1 further comprising an oral care active selected from the group consisting of menthol, methyl salicylate, eucalyptol, thymol, sodium fluoride, sodium monofluorophosphate, stannous fluoride, amine fluorides, water soluble phosphate salts, potassium salts, strontium salts, tooth whitening agents, vitamin A, and mixtures of two or more thereof.

5. The composition of claim 4 wherein said oral care active comprises at least one active selected from the group consisting of menthol, methyl salicylate, eucalyptol, and thymol.

6. The composition of claim 4 wherein said oral care active comprises at least one active selected from the group consisting of sodium fluoride, sodium monofluorophosphate, stannous fluoride, and amine fluorides.

7. The composition of claim 4 wherein said oral care active comprises a tooth whitening agent.

8. The composition of claim 4 wherein the biofilm disruptor comprises 1-decen-3-ol.

9. The composition of claim 8 wherein said carrier is in the form of a mouthwash or mouthrise.

10. The composition of claim 4 wherein said carrier is in the form of a mouthwash or mouthrise.

* * * * *